United States Patent [19]

Jones et al.

[11] Patent Number: 5,037,823
[45] Date of Patent: Aug. 6, 1991

[54] PHARMACEUTICAL COMPOSITIONS FOR RELIEF OF DYSMENORRHEA AND/OR PREMENSTRUAL SYNDROME AND PROCESS

[75] Inventors: Howard Jones, Holmdel; Alison B. Lukacsko, West Windsor; Joseph Migliardi, Mendham, all of N.J.

[73] Assignee: Bristol-Myers Squibb Company, New York, N.Y.

[21] Appl. No.: 452,022

[22] Filed: Dec. 15, 1989

Related U.S. Application Data

[63] Continuation-in-part of Ser. No. 907,698, Sep. 15, 1986.

[51] Int. Cl.5 .................... A61K 31/19; A61K 31/54; A61K 31/185; A61K 31/205
[52] U.S. Cl. ................................ 514/222.8; 514/556; 514/557; 514/570; 514/576
[58] Field of Search ............... 514/557, 556, 576, 570, 514/225, 222.8

[56] References Cited

PUBLICATIONS

Koopmans et al., Eur. J. Clin. Pharmacol (1987) 31:553–557.
Shah et al., Effect of Nonsteroidal Antiinflammatory Drugs (NSAIDS) on Diuretic Property of Hydrochlorothiazide, Indian J. Pharmac. 17:224–8 (1985).

*Primary Examiner*—Stanley J. Friedman
*Attorney, Agent, or Firm*—Charles J. Zeller

[57] ABSTRACT

A pharmaceutical composition for relieving symptoms of dysmenorrhea and/or premenstrual syndrome comprising a combination of ibuprofen and hydrochlorothiazide, and, optionally, an antihistamine.

15 Claims, No Drawings

PHARMACEUTICAL COMPOSITIONS FOR RELIEF OF DYSMENORRHEA AND/OR PREMENSTRUAL SYNDROME AND PROCESS

This is a continuation-in-part application of U.S. Ser. No. 907,698 filed Sept. 15, 1986, now U.S. Pat. No. 4,888,343 issued Dec. 19, 1989.

FIELD OF INVENTION

This invention relates to pharamaceutical compositions useful in the treatment of dysmenorrhea and/or premenstrual syndrome.

BACKGROUND OF INVENTION

Dysmenorrhea is a term used to describe painful menstruation. The pain may range from minor cramping to intense pain accompanied by diarrhea, nausea and vomiting, with sensations of pelvic heaviness and breast fullness. Premenstrual syndrome refers to the tension accruing prior to the onset of menstruation, and is characterized by headaches, nervousness and edema. Once menstruation has begun, there is noticeable polyuria and rapid disappearance of the edema.

Pharmaceutical products for the treatment of dysmenorrhea and/or premenstrual syndrome are known in the prior art and have been marketed commercially. Thus, for example, a number of commercially available products contain a combination of acetaminophen and pamabrom or a combination of acetaminophen, pamabrom and pyrilamine maleate. Products of this character do not contain a non-steroidal anti-inflammatory agent, such as ibuprofen or aspirin, which are highly important but not optimal in relieving the symptoms of dysmenorrhea and/or premenstrual syndrome. The acetaminophen used in such products is known to be an effective analgesic but is not generally recognized as exhibiting significant anti-inflammatory properties.

There is at least one commercial product containing a non-steroidal anti-inflammatory such as aspirin that is marketed for use in treating dysmenorrhea and/or premenstrual syndrome. Disadvantageously, this product does not contain a reliably effective diuretic which, when combined with an effective NSAID, provides relief of the array of symptoms of dysmenorrhea and/or premenstrual syndrome. Thus, this product contains a mixture of aspirin, cinnamedrine and caffeine. Cinnamedrine is conventionally recognized as an antispasmodic. Caffeine, although it is recognized as a diuretic, is not a highly potent diuretic. Moreover, the latter has the disadvantage of inducing sleeplessness in the subjects to whom it is administered, an important consideration for evening utility.

Compositions for use in the treatment of dysmenorrhea, which are disclosed in European Patent Application 0 081 823, are "combinations of analgesics (including prostaglandin synthetase inhibitors such aspirin, indomethacin and ibuprofen), diuretics, antihistamines and antispasmadics." The invention of this European Patent Application is said to reside in also incorporating 5-500 mg dextromethorphan hydrochloride with one or more of: a conventional diuretic such as ammonium chloride, pamabrom and hydrochlorothiazide; a conventional antihistaminic such as pyrilamine maleate; a conventional antispasmodic, for example, cinnamedrine, or a conventional analgesic such as, for example, aspirin, acetaminophen, indomethacin, ibuprofen or naproxen.

G. F. Shah et al, *Effect of Nonsteroidal Antiinflammatory Drugs (NSAIDS) on Diuretic Property of Hydrochlorothiazide*, Indian J. Pharm., 17:224-8 (1985), studied the effects of several NSAIDs including ibuprofen on hydrochlorothiazide (HCTZ) induced changes in urinary volume, sodium, potassium and creatinine excretion, in conscious rats. Shah et al concluded that the diuretic effect as well as the increased urinary sodium and potassium excretion elicited by HCTZ at 2.5 and 5 mg/kg were inhibited after oral administration of NSAIDs such as indomethacin, oxyphenbutazone, ibuprofen and naproxen, in doses which inhibited the rat carrageenin induced hind paw oedema.

Shah et al reports that of the NSAIDs tested, ibuprofen was found to be the most potent in antagonizing diuretic and natriuretic activity. Thus, a dose of 12.5 mg/kg ibuprofen inhibited the diuretic activity of 5 mg/kg HCTZ, while 25 mg/kg ibuprofen significantly antagonized the diuretic activity of 10 mg/kg HCTZ. It is further seen from Table 4 of Shah et al that as the ratio of ibuprofen to HCTZ increased at a constant dose of HCTZ, there was a concomitant reduction in the diuretic activity. For example, at 10 mg/kg HCTZ, the reported diuretic activity is $2.2 \pm 0.16$, while at 10 mg/kg HCTZ and 25 mg/kg ibuprofen, the diuretic activity was $1.6 \pm 0.07$, a reduction of about 28%. Similarly, Shah et al observed like reductions in natriuretic activity.

It is noteworthy that Shah et al administered each of the ibuprofen and the HCTZ in a gum arabic suspension. As pointed out in Bowman & Rand, *Textbook of Pharmacology*, p. 40.10 (2nd Edition 1980), the activity of HCTZ is preparation-dependent. Accordingly, Shah et al's observations are not predictive of the performance of a tablet comprising ibuprofen and HCTZ.

SUMMARY OF THE INVENTION

The present invention involves a composition which contains as the only pharmaceutically active ingredients (a) a non-steroidal anti-inflammatory selected from the group consisting of aspirin and ibuprofen, (b) a diuretic selected from the group consisting of pamabrom and hydrochlorothiazide, and, optionally, (c) an antihistamine, preferably pyrilamine or a pharmaceutically acceptable salt thereof, these ingredients being present at a level in these compositions to afford relief from the symptoms of dysmenorrhea and/or premenstrual syndrome when said compositions are administered to subjects exhibiting these conditions. Pyrilamine has been shown to be a safe and effective calmative, relieving the tension of dysmenorrhea and/or premenstrual syndrome. The compositions of the present invention advantageously contain an effective anti-inflammatory agent, a reliably effective diuretic, and, optionally, an effective calmative.

DETAILED DESCRIPTION OF THE INVENTION

The non-steroidal anti-inflammatory agents useful in the compositions herein disclosed are ibuprofen or aspirin. Combinations of these drugs may also be employed but ordinarily either one or the other will be utilized. The quantity of said anti-inflammatory agent contained in the present composition may be expressed in the form of the daily average dose for this agent, which will vary with anti-inflammatory drug selected. Generally for ibuprofen this will be about 100 to about 2,000 mg/day with the preferred range being about 200 to about 1,200 mg/day. In the case of aspirin the general average daily dose will be about 200 mg/day to about 5 gm/day, the preferred range being about 500 to about 2000 mg/day.

In similar fashion, the quantity of the particular diuretics of use in the present invention and contained in the present products may also be expressed on the basis of the daily average dose for the diuretics (i.e. pamabrom, hydrochlorothiazide or combination thereof), which also will vary with the particular diuretic selected. When the diuretic is hydrochlorothiazide the general average daily dose for this drug provided by the product will be from about 5 to about 250 mg/day and in the case of pamabrom from about 5 to about 500 mg/day. In both cases the preferred range is about 25 to about 200 mg/day.

When the antihistamine (i.e. pyrilamine or its pharmaceutically acceptable salts) is employed in the practice of this invention its level of use is also expressible on the basis of its daily average dose. In this case, the daily average dose will be from about 15 mg to about 400 mg. However, the preferred daily average dose for the antihistamine will fall in the range of from about 30 mg to about 200 mg.

Any of the pharmaceutically acceptable salts of pyrilamine may be utilized in carrying forward the purpose of this invention. By way of example mention may be made of pyrilamine maleate citrate, hydrochloride or sulfate.

The products of this invention will generally be administered in a convenient unit dosage form, preferably in solid dose form such as a tablet, powder, capsule, and the like. The quantity of the respective ingredients that may be contained in this unit dosage form is given in the table below:

|  | Unit Dosage Form | |
| --- | --- | --- |
|  | General Range in mg | Preferred Range in mg |
| Ibuprofen | 50 mg to 800 mg | 100 mg to 400 mg |
| Aspirin | 50 mg to 975 mg | 150 mg to 650 mg |
| Pamabrom | 1 mg to 100 mg | 5 mg to 50 mg |
| Hydrochlorothiazide | 1 mg to 50 mg | 5 mg to 25 mg |
| Pyrilamine Salt | 0 mg to 100 mg | 15 mg to 50 mg |

Optimally each unit dosage form will contain from about 200 mg to about 400 mg of ibuprofen or from about 325 to 500 mg of aspirin.

The prior art Shah et al article demonstrates significantly antagonized diuretic activity of HCTZ when administered in the presence of ibuprofen at ibuprofen/HCTZ ratios of 0.625:1 to 10:1. Surprisingly and unexpectedly, it has been found by Applicants that the diuretic activity antagonism did not worsen as anticipated at higher ratios of ibuprofen to HCTZ, as demonstrated hereinafter with regard to Examples 8 and 9. In the compositions of the present invention, the ratio of ibuprofen to HCTZ is above about 16:1, preferably from about 16:1 to 64:1, most preferably from about 24:1 to 48:1.

In addition to the pharmacologically active ingredients mentioned above, the products of this invention may also contain other excipients. These to a large extent will depend on the nature of the unit dosage form selected for dispensing the present composition.

The present products may be made into capsules, tablets, powders, caplets and may be film coated, enteric coated or formulated into sustained release dosage forms or liquid dosage compositions. When formed into tablets or caplets they may contain adjuvants that facilitate the tableting of the product or enhance its elegance or dissolution rates. Generally illustrative of the adjuvants that may be contained in the various dosage forms encompassed in the present invention are: disintegrating agents, binders, lubricants, fillers, glidents, surfactants, flavoring agents, sweeteners, solvents, liquid carriers, suspending agents, preservatives, etc. More particularly the adjuvants that may be contained in the various dosage forms over and above the active ingredients are as follows:

Caplet and Tablet: Cellulose, lactose, corn starch, stearic acid, water, gelatin, talc, Sterotex, magnesium stearate, terra alba, sucrose, Cab-O-Sil, acacia, etc.

Capsule: spray dried lactose, dimethylsiloxane, corn starch, magnesium stearate, sucrose, Cab-o-Sil, etc.

Liquid Dosage Forms: polyethylene glycol, sucrose, Povidone, sodium citrate, citric acid, flavor, color, quinine, water, etc.

Sustained release compositions may contain such things as glyceryl monostearate, glyceryl distearate, cellulose ethers such as hydroxypropyl methylcellulose and hydroxy propylcellulose, stearic acid, etc.

In general, the products of the present invention may be prepared using the standard technique well known to those skilled in this art, e.g., standard tableting or capsule preparing procedures. However, when pamabrom is utilized as the diuretic and ibuprofen as the non-steroidal anti-inflammatory it has been found advantageous to granulate the pamabrom before mixing it with the ibuprofen. These ingredients, when mixed together in standard procedures, tend to form eutectic mixtures with the result that tablets containing such a mixture become soft upon exposure to stress testing conditions and capsules turned pasty. In addition both of these dosage forms also changed color from white to yellow or orange when prepared using the standard procedures.

When an antihistamine, e.g., pyrilamine maleate, is used in conjunction with the pamabrom and ibuprofen, it is often advantageous to granulate the combination of pamabrom and antihistamine before mixing this combination with the ibuprofen. This mixture, with or without other adjuvants may then be used to prepare the dosage forms, e.g., capsule, tablets.

The products of this invention may be administered using a variety of regimens. Ordinarily the acceptable daily dose will be provided by taking the product twice, three times or four times a day.

The following examples are given to further illustrate the present invention. It is to be understood, however, that the invention is not limited thereto.

The following are the chemical definitions of the materials used in the Examples and identified therein by their trade designations:

Avicel PH 101 and 102: Microcrystalline Cellulose, FMC Inc.

Starch 1500: Pregelatinized starch, Colorcon Inc., West Point, Pa.

Silicone Oil: Dimethicone (U.S.P.), Dimethylpolysiloxane 350 CS, Dow Corning

Tween 80: Polysorbate 80 (CTFA-Cosmetic Ingredient Dictionary, Third Edition, p. 247)

Cab-0-Sil: Fumed Silica, Cabot, Inc.

Povidone: Polyvinyl pyrrolidone, GAF Corp.

Crospovidone XL10: Cross linked Polyvinylpyrrolidone, GAF Corp.

The "Ibuprofen Granulation" used in Examples 5 and 6 below is prepared by first mixing ibuprofen (200 mg) and corn starch (50 mg). An aqueous granulating solution, prepared containing Povidone K29-32 (6 mg), Avicel PH 101 (41.5 mg) and Crospovidone XL-10 (1.5 mg), was used to granulate the ibuprofen/starch mixture.

EXAMPLE 1

| Ibuprofen/Pamabrom/Pyrilamine Maleate: Capsules Formula CE 3375-70 | |
|---|---|
| Ingredients | Amount Per Dose |
| a. Ibuprofen | 150.00 mg |
| b. Pamabrom | 25.00 mg |
| c. Pyrilamine Maleate | 15.00 mg |
| d. Avicel pH 101 | 50.00 mg |
| e. Starch 1500 | 117.50 mg |
| f. Silicon Oil | 2.00 mg |
| g. Tween 80 | 0.50 mg |
| h. Cab-O-Sil | 0.25 mg |
| | 360.25 mg |

Method
A. Blend b, d and 30 mg e
B. Dissolve c in water and use to granulate A, then dry
C. Blend 87.5 mg e, f and g
D. Blend B, C, a and h. Fill into size #1 capsules

EXAMPLE 2

| Ibuprofen/Pamabrom: Capsules Formula CS 3570-05 | |
|---|---|
| Ingredients | Amount Per Dose |
| a. Ibuprofen | 150.00 mg |
| b. Pamabrom | 25.00 mg |
| c. Avicel pH 101 | 82.50 mg |
| d. Starch 1500 | 90.00 mg |
| e. Silicon Oil | 2.00 mg |
| f. Tween 80 | 0.50 mg |
| | 350.00 mg |

Method:
A. Mix b, 50 mg d and 42.5 mg c, granulate with water and dry
B. Mix 40 mg d, e and f
C. Mix A, B, a and 40 mg c
D. Fill C into size #1 capsules

EXAMPLES 3 AND 4

| Ibuprofen/Hydrochlorothiazide HCl: Capsule | | |
|---|---|---|
| | Example 3 Formula CS 3570-14 | Example 4 Formula CS 3570-31 |
| Ingredients | Amount Per Dose | Amount Per Dose |
| a. Ibuprofen | 200.00 mg | 300.00 mg |
| b. Hydrochlorothiazide HCl | 12.50 mg | 12.50 mg |
| c. Starch 1500 | 134.50 mg | 183.50 mg |
| d. Silicon Oil | 2.00 mg | 2.80 mg |
| e. Tween 80 | 0.50 mg | 0.70 mg |
| f. Cab-O-Sil | 0.50 mg | 0.50 mg |
| | 350.00 mg | 500.00 mg |

Method:
A. Blend all ingredients
B. Fill blends for CS3570-14 into size #1 capsules and for CS3570-31 into size #0 capsules.

EXAMPLE 5

| Ibuprofen/Pamabrom/Pyrilamine Maleate Tablets | |
|---|---|
| Ingredients | Formula CS 3570-34 Amount Per Dose |
| a. Pamabrom | 25.00 mg |
| b. Pyrilamine Maleate | 15.00 mg |
| c. Starch 1500 | 75.00 mg |
| d. Povidone, USP (K29-32) | 0.75 mg |
| e. Hydroxypropyl methylcellulose E5-Premium | 4.11 mg |
| f. Propylene Glycol | 0.90 mg |
| g. Ibuprofen Granulation (Equivalent to 150 mg Ibuprofen) | 224.24 mg |
| h. Silicon Oil | 2.00 mg |
| i. Tween 80 | 0.50 mg |
| j. Starch 1500 | 35.00 mg |
| | 382.50 mg |

Method:
A. Blend a, b and c, granulate with water and dry
B. Dissolve d, e and f in water and use to spray coat A
C. Blend h, i and j
D. Blend B, C and g and compress into tablet

EXAMPLE 6

| Ibuprofen/Pamabrom/Pyrilamine Maleate Tablets | |
|---|---|
| Ingredients | Formula CS 3570-32 Amount Per Dose |
| a. Pamabrom | 25.00 mg |
| b. Pyrilamine Maleate | 15.00 mg |
| c. Avicel PH 101 | 50.00 mg |
| d. Povidone, USP (K29-32) | 6.74 mg |
| e. Hydroxypropyl methylcellulose E5-Premium | 6.63 mg |
| f. Propylene Glycol | 1.24 mg |
| g. Ibuprofen Granulation (Equivalent to 150 mg Ibuprofen) | 224.24 mg |
| h. Starch 1500 | 35.00 mg |
| i. Silicone Oil | 2.00 mg |
| j. Tween 80 | 0.50 mg |
| | 366.35 mg |

Method
A. Blend a, b and c
B. Dissolve 5.6 mg d in water and use to granulate A, then dry
C. Dissolve 1.14 mg d, e and f in water and use to spray coat B
D. Blend h, i and j
E. Blend C, D and g and compress into tablet

EXAMPLE 7

| Ibuprofen/Hydrochlorothiazide HCl Tablets | |
|---|---|
| Ingredients | Formula CS 3570-15 Amount Per Dose |
| a. Ibuprofen | 200.00 mg |
| b. Corn Starch NF | 50.00 mg |
| c. Povidone, K29-32 | 6.00 mg |
| d. Avicel PH 101 | 41.50 mg |
| e. Avicel PH 102 | 136.50 mg |
| f. Hydrochlorothiazide HCl, USP | 12.50 mg |
| g. Crospovidone XL10 | 2.50 mg |
| h. Cab-O-Sil | 0.50 mg |
| i. Magnesium Stearate | 0.50 mg |
| | 450.00 mg |

Method:
A. Blend all ingredients geometrically
B. Compress into tablets

EXAMPLE 8

A preclinical diuretic efficacy study was conducted in two stages (Experiments A and B), the experiments being run fifteen days apart and each experiment lasting two days.

In Experiment A, five doses of hydrochlorothiazide (HCTZ) ranging from 0.25 to 4 mg/kg were tested, while in Experiment B, four doses of HCTZ ranging from 1.5 to 12 mg/kg were used and coadministered with a constant dose of 96 mg/kg ibuprofen.

Also tested in Experiment A was a control containing no actives (vehicle only), and also tested in Experiment B was a first control containing no actives and a second control containing 96 mg/kg ibuprofen.

Ten male Wistar rats were used per dose in each experiment. The rats were fasted overnight prior to testing and during testing. After the study dose (or vehicle) was administered, each animal was given a hydrating dose of normal saline (30 ml/kg). Each rat was placed in an individual cage and urine collected for five hours. Total urinary volume, total urinary sodium and potassium excretion, and urinary pH were determined, which parameters were analyzed as ml/kg body weight, mEq/kg body weight, and pH, respectively.

The results of the tests are provided below.

|  | Volume (ml/kg) | Na (mEq/kg) | K (mEq/kg) | pH |
|---|---|---|---|---|
| Experiment A | | | | |
| HCTZ (mg/kg) | | | | |
| 0 | 18.69 | 2.53 | 0.73 | 5.72 |
| 0.25 | 23.17 | 3.47 | 0.80 | 5.78 |
| 0.50 | 22.01 | 3.33 | 0.95 | 5.76 |
| 1.0 | 28.61 | 4.09 | 0.97 | 5.61 |
| 2.0 | 32.91 | 5.20 | 1.16 | 5.26 |
| 4.0 | 37.04 | 5.29 | 1.58 | 5.64 |
| Experiment B | | | | |
| HCTZ (mg/kg) w/96 mg/kg Ibuprofen | | | | |
| 0 w/o Ibuprofen | 20.24 | 2.93 | 0.80 | 6.11 |
| 0 w/Ibuprofen | 12.61 | 1.49 | 0.55 | 6.22 |
| 1.5 | 22.98 | 3.57 | 1.19 | 6.06 |
| 3.0 | 17.08 | 2.92 | 0.99 | 5.98 |
| 6.0 | 22.97 | 3.66 | 1.08 | 5.75 |
| 12.0 | 26.37 | 4.42 | 1.22 | 6.05 |

The urinary excretion data from Experiment A demonstrate a clear-cut dose response for HCTZ. The data collected for the two controls (—O— mg HCTZ w/o ibuprofen and —O— mg HCTZ w/ibuprofen) in Experiment B illustrate the extent to which ibuprofen itself causes urinary concentration. The data reflect urinary excretion of sodium and potassium, and reduced volume. Unexpectedly, when combined with ibuprofen, the diuretic efficacy of HCTZ is exhibited as increased urinary volume, as well as the content of sodium and potassium. In Shah et al, a significant inhibition of diuresis was observed at the 5:1 ibuprofen/HCTZ ratio. To the contrary, in these studies above the antidiuretic efficacy of ibuprofen was significantly offset at ratios of ibuprofen to HCTZ of 16:1 to 64:1.

EXAMPLE 9

A single blind, randomized, four-treatment, four-period crossover study of ibuprofen and hydrochlorothiazide (HCTZ) interaction was conducted with 16 female human adults. The study medications were: (a) a placebo, (b) 12.5 mg HCTZ, (c) 400 mg ibuprofen, and (d) in combination, 400 mg ibuprofen and 12.5 mg HCTZ (32:1 ibuprofen/HCTZ ratio).

Alcohol consumption was not permitted for 48 hours before dosing; caffeine was restricted for 24 hours before dosing. The test subjects were held to a controlled diet with fluid intake, sodium and potassium restricted.

Urine was collected and pooled for 24 hours prior to each drug, and was collected voluntarily from the test subjects at 1, 2, 3, 4, 5, 6, 9, 12, 15 and 24 hours post treatment.

The 6- and 24-hour urinary excretion data is reported below.

| Medication | Urine Volume (ml) | Na Excretion (mEq) | K Excretion (mEq) |
|---|---|---|---|
| Cumulative 6-Hour Urinary Excretion | | | |
| (a) Placebo | 935 | 44 | 14.2 |
| (b) 12.5 mg HCTZ | 1405 | 98 | 19.3 |
| (c) 400 mg Ibuprofen | 799 | 29 | 11.9 |
| (d) 400 mg Ibuprofen 12.5 mg HCTZ | 1165 | 76 | 17.7 |
| Cumulative 24-Hour Urinary Excretion | | | |
| (a) Placebo | 2172 | 157 | 45.0 |
| (b) 12.5 mg HCTZ | 2681 | 193 | 45.5 |
| (c) 400 mg Ibuprofen | 2078 | 138 | 39.5 |
| (d) 400 mg Ibuprofen 12.5 mg HCTZ | 2641 | 190 | 43.5 |

Shah et al observed approximately a 25% decrease in diuretic activity at ibuprofen/HCTZ ratios of 5:1 and 10:1. Given a typical dose response, one of ordinary skill in the art would anticipate logically that inhibition of urinary activity would be greater as the ibuprofen/HCTZ ratio increased. Unexpectedly, the data above demonstrate that the anticipated dose response does not occur. Thus, at the end of the 6-hour period, the suppression in urine volume was only 17%. After 24 hours the urine output of those test subjects taking the ibuprofen/HCTZ medication was essentially no different from those taking HCTZ only——up about 23% compared to placebo. Those test subjects taking ibuprofen alone had a suppression in urine output of 12% as compared to placebo over the 24-hour period. Similarly, after 24 hours the sodium excretion level for the ibuprofen/HCTZ dosing is about the same as for HCTZ alone, while ibuprofen alone had a 34% decrease, all as compared to the placebo.

Extrapolation of the data in Shah et al would suggest total inhibition of HCTZ-induced natriuresis at the 32:1 ibuprofen/HCTZ ratio. Unexpectedly, this was clearly not the case in the clinical studies reported on above. Moreover, the excretion of $Na^+$ without concomitant equivalent loss of $K^+$ as observed herein provides a safety advantage for the ibuprofen/HCTZ combination reported on above.

What is claimed is:

1. A pharmaceutical composition for the relief of dysmenorrhea and/or premenstrual syndrome in humans containing in unit dose form essentially the only pharmacologically active ingredients about 50 to about 800 mg ibuprofen and about 1 to about 50 mg of hydrochlorothiazide, said pharmaceutically active ingredients being present in said composition in amounts sufficient to afford relief from the symptoms of dysmenorrhea and/or premenstrual syndrome with the ibuprofen/hydrochlorothiazide weight ratio being from about 16:1 to about 64:1, said composition further containing an antihistamine at an antihistaminicly calmative effective level.

2. The composition of claim 1 wherein the unit dosage form contains from about 100 to about 400 mg ibuprofen and from about 5 to about 25 mg hydrochlorothiazide.

3. The composition of claim 1 or 2 wherein the ibuprofen/hydrochlorothiazide ratio is from about 24:1 to about 48:1.

4. The composition of claim 1 or 2 wherein the unit dosage form contains from about 15 to about 50 mg antihistamine.

5. The composition of claim 4 wherein the ibuprofen/hydrochlorothiazide ratio is from about 24:1 to about 48:1.

6. The composition of claim 5 wherein said antihistamine is pyrilamine maleate.

7. The composition of claim 4 wherein said antihistamine is pyrilamine maleate.

8. The composition of claim 1 or 2 wherein the ibuprofen/hydrochlorothiazide ratio is about 32:1.

9. The composition of claim 7 wherein the ibuprofen/hydrochlorothiazide ratio is 32:1.

10. The composition of claim 1 or 2, including a pharmaceutical carrier.

11. A process for relieving symptoms of dysmenorrhea and/or premenstrual syndrome in a human subject exhibiting such symptoms comprising administering to said subject a composition of claim 1 in an amount sufficient to relieve said symptoms.

12. The process of claim 11 wherein the unit dose form is administered one to six times daily.

13. The process of claim 12 wherein the ibuprofin/hydrochlorothiazide ratio in the composition is from about 24:1 to about 48:1.

14. The process of claim 1 wherein the unit dose form is administered two to four times daily.

15. The process of claim 14 wherein the ibuprofen/hydrochlorothiazide ratio is 32:1.

* * * * *